United States Patent
Onose

(10) Patent No.: US 8,409,855 B2
(45) Date of Patent: Apr. 2, 2013

(54) APPARATUS FOR PRODUCING FEEDS COMPRISING DRIED AND FERMENTED ANIMAL AND PLANT RESIDUES AND DRIED AND FERMENTED FERTILIZERS

(75) Inventor: Kazuhiro Onose, Hokkaido (JP)

(73) Assignee: Hokkaido Tokushushiryou Kabushikikaisha, Hokkaido (JP)

( * ) Notice: Subject to any disclaimer, the term of this patent is extended or adjusted under 35 U.S.C. 154(b) by 0 days.

(21) Appl. No.: 13/594,960

(22) Filed: Aug. 27, 2012

(65) Prior Publication Data
US 2012/0322143 A1 Dec. 20, 2012

Related U.S. Application Data

(63) Continuation-in-part of application No. 12/601,075, filed as application No. PCT/EP2008/059598 on May 19, 2008, now abandoned.

(30) Foreign Application Priority Data

May 23, 2007 (JP) .................. 2007-163142

(51) Int. Cl.
*C12M 1/02* (2006.01)
*C12M 3/00* (2006.01)

(52) U.S. Cl. ............... 435/303.3; 435/303.1; 435/303.2; 435/290.1; 435/290.2; 435/290.3

(58) Field of Classification Search .... 435/290.1–290.3, 435/303.3, 303.1, 303.2, 289.1
See application file for complete search history.

(56) References Cited

U.S. PATENT DOCUMENTS 2,878,112 A * 3/1959 Morrison ............................. 71/9

* cited by examiner

*Primary Examiner* — Michael Marcheschi
*Assistant Examiner* — Shanta G Doe
(74) *Attorney, Agent, or Firm* — Abelman, Frayne & Schwab

(57) ABSTRACT

An apparatus is provided for the producing feeds/fertilizers containing died and fermented animal and plant residues. The apparatus includes a fermentation tank, an unobstructed circulation duct connected to the fermentation tank and a blower directly connected to the circulation duct wherein blower supplies air for advancing the residues up the circulation duct.

1 Claim, 1 Drawing Sheet

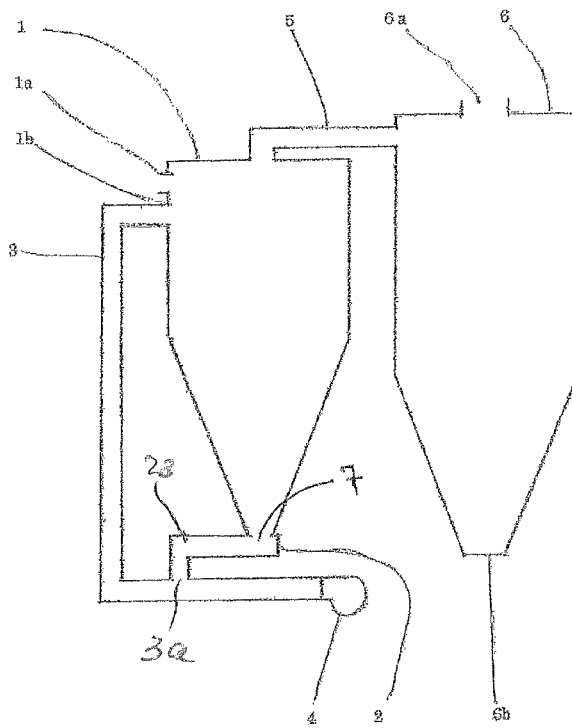

APPARATUS FOR PRODUCING FEEDS COMPRISING DRIED AND FERMENTED ANIMAL AND PLANT RESIDUES AND DRIED AND FERMENTED FERTILIZERS

RELATED APPLICATION

This application is a continuation-in-part of application Ser. No. 12/601,075 filed Nov. 20, 2009 now abandoned, which is a National Stage Application of International Application PCT/EP2008/059598 filed May 19, 2008 that claims priority of Japanese Application 2007-163142 filed May 23, 2007, all of the three applications being incorporated herein by reference thereto.

BACKGROUND OF THE INVENTION

1. Field of the Invention

The present invention relates to an apparatus for producing feeds comprising dried and fermented animal and plant residues and dried and fermented fertilizers having a function of making organic wastes into feeds, fertilizers and the like.

2. Description of the Prior Art

A lot of proposals have been made on treatment systems of organic wastes, but initial investments and running costs are expensive, the organic wastes are hardly reused, and the proposals cannot be considered to be well functioning.

A lot of proposals have been also made on methods and devices for fermentation/drying, and they can be roughly divided into three groups.

A first group is a method of natural fermentation using flat arranging, turning over and the like, the second group is a heating/agitation type device, and the third group is a method for fermentation and drying using a decompressed drying device.

Prior-art methods using natural fermentation requires a long time till feeds/fertilizers are completed and also requires a large workshop, oxygen supply/temperature control by repeated turning over, and this is not efficient in terms of time and a working cost.

With the heating/agitating type devices, heating costs are high, chances/areas where treatment objects are in contact with air are small in agitation, which is not suitable for evapotranspiration, and energy efficiency is poor.

With the decompressed drying type devices, too, the heating costs are high, initial investment is large, and a temperature control inside a plant to a state suitable for fermentation is difficult.

SUMMARY OF THE INVENTION

In order to solve the above problems, the present invention is characterized in that an evapotranspiration action is efficiently conducted by mixing an auxiliary material for adjusting a fermentation environment in an animal and plant residues having been finely cut out/crushed or adding a known fermenter to the animal and plant residues not requiring the auxiliary material such as sake lees, beer lees, tofu lees and the like and then, inputting the residues into a fermentation tank of the apparatus for producing feeds comprising dried and fermented animal and plant residues and dried and fermented fertilizers, reserving and accumulating it and then, transferring it to a circulation duct in a small and constant amount while agitating it by a screw conveyer from the lowermost part, blowing it up in the circulation duct with hot air at a temperature of approximately 40 to 50 degrees using air from a blower or the like or waste heat of a boiler or the like and emitting/spraying it into the air in a space in the fermentation tank through a circulation input located at an upper part so as to increase an area in contact with the air and to increase chances in contact with the air through repeated circulation in the apparatus.

By repeating emission/spraying into the air of the animal and plant residues through blowing up with air or hot air using a blower or the like, oxygen required for fermentation is uniformly supplied, characteristics for keeping the fermentation environment are favorable, and good-quality dried and fermented feeds/dried and fermented fertilizers and the like can be manufactured.

Since the apparatus for producing feeds comprising dried and fermented animal and plant residues and dried and fermented fertilizers has a simple structure not requiring a large installation area and can suppress initial investment and running costs, too, by efficiently performing an evapotranspiration action as compared with heated drying and decompressed drying and has characteristics to maintain the fermentation environment favorable by uniform supply of oxygen, uniform fermentation can be realized, and since drying at 60° C. or less is possible, extinction rate of fermenters is lower than that of the heated drying or decompressed drying dried at a high temperature, and the good-quality dried and fermented feeds/dried and fermented fertilizers and the like with stable nutrition value/high digestibility can be manufactured. Also, an inexpensive transport cost can be realized by drying to a moisture content of 10% as compared with fermented feeds and fertilizers usually containing a moisture content of approximately 50%, contribution can be made to prevention of quality alteration and to improvement of a distribution cost, which have been great obstacles to reuse of organic wastes, and since direct warming/heating by fossil fuels or the like is not used but only steam is emitted other than the product, and no discharged water/waste liquid is produced at all, contribution can be made to environmental preservation of the earth.

BRIEF DESCRIPTION OF THE DRAWINGS

In the drawings:

Single FIGURE of the drawings shows a schematic view of an apparatus according to the present invention for producing feeds comprising dried and fermented animal and plant residues and dried and fermented fertilizers of the present invention.

DETAILED DESCRIPTION OF THE PREFERRED EMBODIMENT

According to the present invention, efficient/economical drying using fermentation heat of organic wastes is realized by a simple combination of a fermentation tank, a screw conveyer, a blower, a duct, and a product reception tank.

A preferred embodiment of the present invention will be described referring to the attached drawing FIGURE. As shown in the FIGURE, an apparatus for producing feeds comprising dried and fermented animal and plant residues and dried and fermented fertilizers has a fermentation tank 1 having an inlet 1a provided at its upper part for receiving animal and plant residues, and circulation outlet 7 provided at its lower part. An unobstructed circulation duct 3 connects the upper part of the fermentation tank 1 with the lower part of the fermentation tank 1. A conduit 2a connects the circulation duct 3 with the circulation outlet 7 of the fermentation tank 1. The circulation duct 3 is connected with the conduit 2a at a connection point 3a spaced from the circulation outlet 7 of the fermentation tank 1. At its upper part, the circulation duct 3 has a circulation inlet 1b communicating with the fermentation tank 1. A screw conveyor 2 is located in the conduit 2a for delivering residues from the circulation outlet 7 of the fermentation tank 1 to the connection point 3a of the circulation duct 3 with the conduit 2a. A blower 4 is located at the lower end of the circulation duct 3 behind the connection point 3a for supplying air for advancing the residues up the circulation duct with a generated air stream and for providing fermentation oxygen. The blower 4 is directly connected with the circulation duct 3. The apparatus further includes a product reception tank 6, and a discharge conduit 5 that connects the fermentation tank 1 with the reception tank 6. The shapes, materials, scales, arrangements and the like described above are matters of design, and other shapes, scales, and arrangements may be used as long as they are within a range of the present invention and do not depart therefrom, and a blower can create air for blowing up such as a blower, a fan, a forage blower, a snow blower and the like, and any duct can be also used for the circulation duct as long as it forms a circulation passage such as a pipe, a hose, a chimney and the like.

An auxiliary material is mixed in the animal and plant residues having been finely cut out, a fermenter is added, and then, the residues are inputted into the fermentation tank 1 through the inlet 1a of animal and plant residues, reserved and accumulated and then, transferred to the circulation duct 3 by the screw conveyer 2 at the lower part, the inside of the circulation duct 3 is blown up together with air by the blower 4, emitted and sprayed into the air in a space in the fermentation tank 1 through the circulation inlet 1b, reserved and accumulated again, and repeatedly circulated within the apparatus.

The dried and fermented animal and plant residues and dried and fermented fertilizers having been fermented, dried and become a product during circulation are transferred and separately contained in the product reception tank 6 with discharged air from the discharge duct 5, while the discharged air is discharged from a discharge outlet 6a at the top part.

The present invention has characteristics that chances and areas in contact with air are increased, an evapotranspiration action is performed efficiently, and no external heat source is required by using fermentation heat of the animal and plant residues and emitting/spraying the animal and plant residues generating heat into the air in a space in the fermentation tank.

Byproducts of food processing contain much moisture and are difficult to be reserved, and they need to be dried for distribution. However, a prior-art drying method using fossil fuels is not economical and the present invention can be used as an alternative inexpensive method.

What is claimed is:

1. An apparatus for producing feeds/fertilizers containing dried and fermented animal and plant residues, the apparatus comprising:

a fermentation tank having an inlet for animal and plant residues, a circulation inlet provided in an upper part thereof, a circulation outlet provided in a bottom part thereof, and a discharge outlet provided in the upper part thereof;

an unobstructed circulation duct connected at an upper end thereof with the circulation inlet and at a lower end thereof with the circulation outlet of the fermentation tank at a connection point spaced from the circulation outlet;

a screw conveyor located beneath the circulation outlet of the fermentation tank for transferring residues from the circulation outlet of the fermentation tank to the connection point of the circulation duct with the circulation outlet;

a blower located at the lower end of the circulation duct behind the connection point of the circulation duct with the circulation outlet of the fermentation tank and directly connected with the circulation duct for supplying air for advancing the residues up in the circulation duct with a generated air stream and for providing fermentation oxygen, the generated air stream being a sole source for advancing the residue up the circulation duct;

a product reception tank having an air inlet for receiving dried fermented residues, an air discharge outlet, both the inlet and the air discharge outlet being located in an upper part of the product reception tank and a discharge outlet for discharging the dried and fermented residue; and a discharge duct connecting the inlet of the product reception tank with the discharge outlet of the fermentation tank, the fermented and dried residues being transmitted from the fermentation tank to the product reception tank with discharge air flowing through the discharge duct.

* * * * *